United States Patent [19]
Hayashi et al.

[11] Patent Number: 5,229,839
[45] Date of Patent: Jul. 20, 1993

[54] METHOD AND APPARATUS FOR MEASURING THE SIZE OF A SINGLE FINE PARTICLE AND THE SIZE DISTRIBUTION OF FINE PARTICLES

[75] Inventors: Shigeru Hayashi; Shoji Horiuchi, both of Chofu, Japan

[73] Assignee: National Aerospace Laboratory of Science & Technology Agency, Tokyo, Japan

[21] Appl. No.: 795,269

[22] Filed: Nov. 20, 1991

Related U.S. Application Data

[63] Continuation of Ser. No. 418,307, Oct. 6, 1989, abandoned.

[51] Int. Cl.$^5$ .................. G01N 15/02; G01N 21/00
[52] U.S. Cl. .......................... 356/336; 356/340; 356/343; 356/364
[58] Field of Search .............. 356/335–343, 356/351, 364, 368; 250/574, 576, 564

[56] References Cited

U.S. PATENT DOCUMENTS 3,612,689 10/1971 Liskowitz ..................... 356/364
3,901,602 8/1975 Gravatt ........................ 356/364

FOREIGN PATENT DOCUMENTS 0044646 2/1987 Japan ........................... 356/336

OTHER PUBLICATIONS

Powder Metallogy Int'l, vol. 10, No. 2 May 1978 p. 98.

*Primary Examiner*—Richard A. Rosenberger
*Assistant Examiner*—Hoa Q. Pham
*Attorney, Agent, or Firm*—Armstrong, Westerman, Hattori, McLeland & Naughton

[57] ABSTRACT

The invention relates to a method and an apparatus for determining the size or the size distribution of fine particles. A single particle or a group of particles are shone by a parallel polarized beam of a single wave length and the scattered intensity on the plane of polarization of the incident beam is measured by a photodetecting array. For a single particle the size is determined from the peak scattering angle at which the profile of the product of the scattered intensity and the scattering angle has the peak. On the other hand, for a group of particles, the size distribution is determined from the angular variation of the scattered intensity or the profile of the product of the scattered intensity and the scattering angle measured on the plane of polarization of the incident beam. For fine particles mixed with large particles the scattered intensities on the plane at a right angle to the plane of polarization measured by another photodetecting array is used to improve the accuracy of size determination of the fine particles.

8 Claims, 3 Drawing Sheets

FIG. 4(a) $D_P \gg \lambda$ 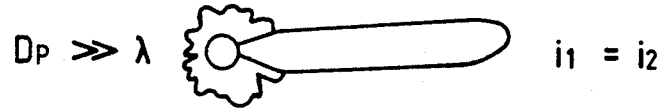 $i_1 = i_2$
FIG. 4(b) $D_P \sim \lambda$ 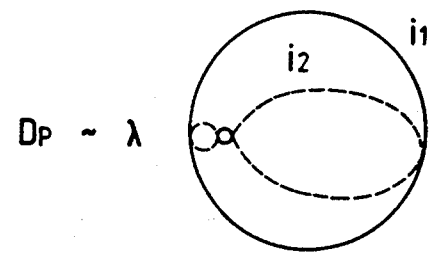
FIG. 4(c) $D_P \ll \lambda$ 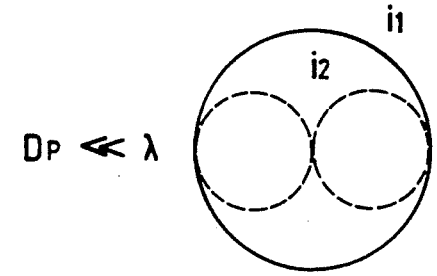

METHOD AND APPARATUS FOR MEASURING THE SIZE OF A SINGLE FINE PARTICLE AND THE SIZE DISTRIBUTION OF FINE PARTICLES

This application is a continuation of U.S. patent application Ser. No. 418,307 filed Oct. 6. 1989 now abandoned.

BACKGROUND OF THE INVENTION

1. Field of the Invention

This invention relates to a method and an apparatus for determining the size of a single fine particle and the size distribution of a group of fine particles.

2. Description of the Prior Art

Recently, submicron particles are widely used in manufacturing advanced ceramics, super-conductive materials, magnetic materials, pigments etc. Accurate determination of the size or size distribution of these fine particles are desired more than ever.

For the size determination of particles larger than one micron, diffraction-based instruments is widely used. In these instruments, the scattered light from a group of particles illuminated by a parallel laser beam is collected by an optical lens placed forwardly and the angular distribution of the intensity of the scattered light is detected by a photodetecting array placed on the focal plane of the lens. The measured angular distribution of the scattered intensity is analyzed to determine the size distribution based on the diffraction theory for light scattering by spherical particles. The accuracy of sizing deteriorates with decreasing size. For submicron particles, the diffraction-based instruments can not be used.

Mie's light scattering theory quantitatively described the angular variation of the intensity of light scattered from a spherical particle. For a particle of diameter D much larger than the wavelength of the incident beam $\lambda$ ($D \gg \lambda$) most of the scattered energy is concentrated into a forward sharp cone, as can be seen in FIG. 3 (a). On the other hand, for particles of size comparable to or smaller than the wavelength of light, a large portion of the scattered energy is directed sidewards and backwards as shown in FIG. 3 (b) and 4 (c).

In the actual measurement, the scattered intensity at angles very close to zero can not be measured with accuracy because of the smearing caused by imperfection of the collecting lens, the fluctuation of wavelength of the light source and spatial nonuniformity of the refractive index of the surrounding medium or the like but also due to the restriction that the incident beam cannot be focused into a spot which is smaller than the diffraction limit of the lens. The size distribution obtained is distorted by the inaccuracy in the measured scattered intensity.

One of the present inventors has shown that the influence of the smearing on the size determination can be reduced by analyzing the profile of $I(\theta)\theta$, the product of the measured scattered intensity $I(\theta)$ and the scattering angle $\theta$, rather than $I(\theta)$. The $I(\theta)\theta$ at angles near zero is small and the measurement error in $I(\theta)$ has little influence on the determination of size distribution. For a single particle the $I(\theta)\theta$ profile has a peak at a specific angle determined by the ratio of the particle size to the wavelength. This peak scattering angle almost monotonously increases as the particle size decreases and is very sensitive to the change of particle size. Therefore, the particle size can be determined with accuracy from the peak scattering angle along, even for the incident beam which has a plane of polarization which changes with time. However, when the particle size becomes comparable to or smaller than the wavelength of light, the peak disappears and, as a result, the particle size cannot be determined by the above mentioned method. For a group of these fine particles, the distribution of particle size cannot be measured with accuracy.

SUMMARY OF THE INVENTION

This invention provides a method and an apparatus which can be used in the accurate at any time of either the size of a single fine particle or the size distribution of a group of particles which are comparable to or smaller than the wavelength of light.

According to this invention, a parallel polarized beam of monochromatic light illuminates a single fine particle or a group of particles which are comparable to or smaller than the wavelength of light in size, the angular variation of the scattered intensity $I_{2(\theta)}$ is measured on the plane of polarization of said illuminating beam.

For a single fine particle or a group of mono-sized particles, however fine they may be, the particle size can be determined from the peak scattering angle at which the profile of the product of the intensity of scattered light and the scattering angle has the peak.

For a group of particles with a size distribution, the profile of the product of the scatted intensity and the scattering angle is the summation of the profiles from each particle in the group. Therefore, the size distribution is determined by analyzing the measured intensity profile for the group of particles.

Furthermore, even for a mixture composed of particles smaller and much larger in comparison to the wavelength of light, the size distribution of the smaller particles can be determined with high accuracy. The contribution of the larger particles is removed by analyzing the difference between or the ratio of the intensities of scattering light on the plane of polarization and on the plane at a right angle thereto.

Such a determination is accomplished by a light source for producing a parallel polarized beam having a single wavelength, photodetecting arrays disposed on the same plane as the plane of polarization of the incident beam and on the plane perpendicular thereto, and an operation circuit for processing the output signals from said photo-detecting arrays.

BRIEF DESCRIPTION OF THE DRAWINGS

FIG. 4 shows the variation of polar diagram of scattered intensity with particle size for particle sizes which are respectively larger, equal to, and smaller than the wavelength of light;

DETAILED DESCRIPTION OF THE PREFERRED EMBODIMENTS

Figure 1:
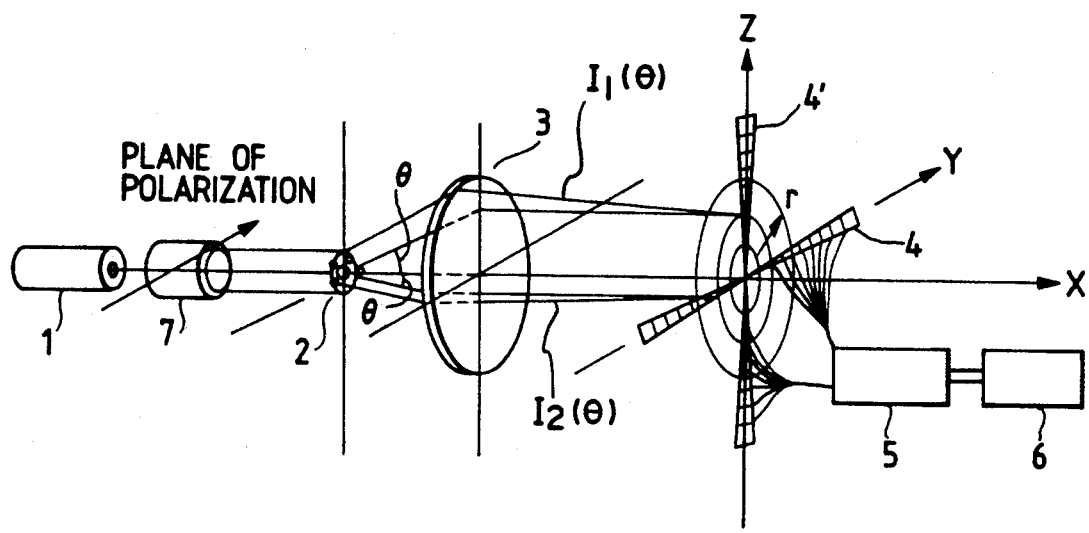
FIG. 1 is a conceptual view of one embodiment of the apparatus for carrying out the size determination according to this invention.
Figure 2:
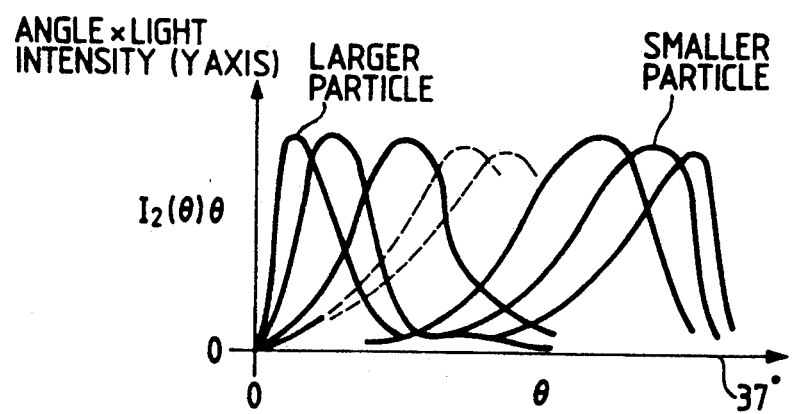
FIG. 2 is a graphic representation showing the variation of an $i_2(\theta)\theta$ profile with particle size, $i_2(\theta)$ being the scattered intensity on the plane of polarization of the incident beam.
Figure 3A:
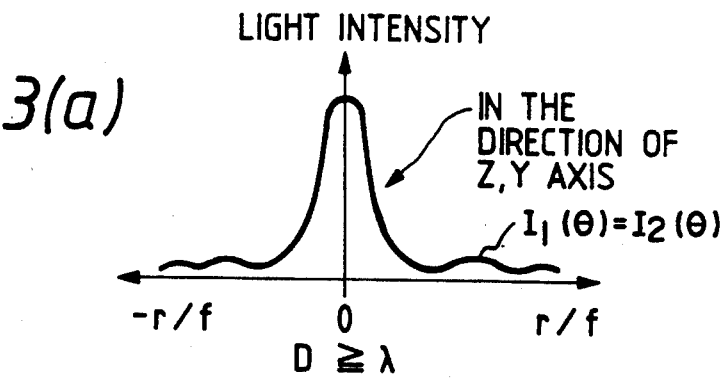
FIGS. 3 (a) and 3 show the angular distributions of the intensities of polarized components of the forwardly scattered light for particles much smaller and larger than the wavelength of light.
Figure 3B:
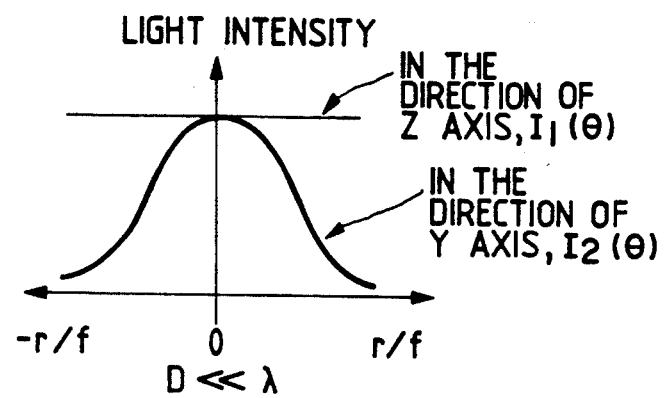

Embodiments of this invention are described hereinafter. FIG. 1 shows one embodiment of the apparatus for carrying out the particle size measurement according to this invention. A helium-neon laser (1) emitting a linearly polarized beam is used to illuminate a group of particles (2). The light scattered forwardly is converged on the focal plane by a convergent lens (3) according to its scattering angle. A beam expander (7) is used to expand the width of the beam for a group of particles having a spatial extent.

On the aforesaid convergent plane, two arrays consisting of photoelectric conversion elements are arranged; one (4) is for detecting the intensity of the scattered light on the plane of polarization of the incident beam, $I_2(\theta)$, and another (4') is photoelectric conversion elements for the intensity on the perpendicular thereto, $I_1(\theta)$. The signals according to the scattered intensity in each direction are outputted. These signals are processed to output necessary information by an operation circuit to detect the peak scattering angle or by comparator circuits (5) and (6).

FIG. 4 (a) schematically shows the variation of the scattered intensity with particle size. More specifically, for a particle of size $D_p$ sufficiently larger than the wavelength of the incident beam $\lambda$, the scattered intensity is high merely at extremely narrow forward scattering angles as shown in FIG. 4 (a), and the difference between intensities $i_2(\theta)$ and $i_1(\theta)$ is negligible small.

For a particle of size sufficiently smaller than the wavelength of the incident beam, the intensity $i_1$ is nearly independent of scattering angle while the intensity $i_2$ is dependent upon the scattering angle, as illustrated in FIG. 4 (c). This is the reason why in the $I(\theta) \cdot (\theta)$ profile the peak disappears for sufficiently fine particles. It is noted that $I(\theta)$ is the summation of $I_1(\theta)$ and $I_2(\theta)$. However, the $I_2(\theta)\theta$ profile continues to have the peak even for infinitely small particles. For example, for a particle of 0.05 micron in size illuminated by an incident beam having a wavelength of 0.6328 microns from a helium neon laser, the $i_2(\theta)\theta$ profile has a peak at approximately 37 degrees. From the value of this peak scattering angle the particle size is determined accurately. For a particle of size comparable to the wavelength of the incident beam, the angular distribution of the scattered intensity is intermediary as shown in FIG. 4 (b).

Figure 5:
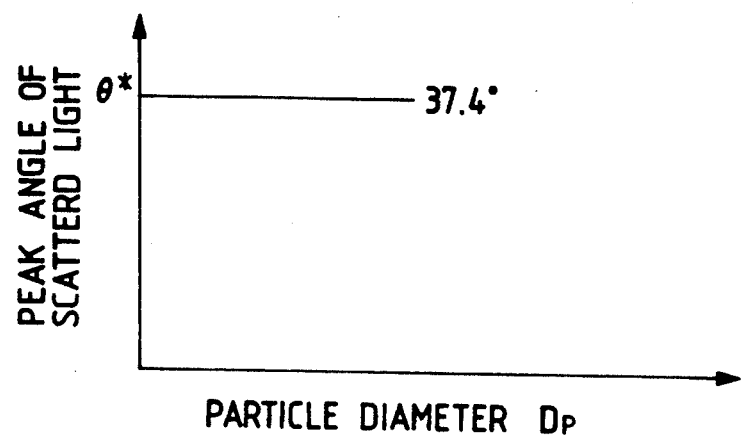
FIG. 5 is a graphic representation showing the variation of the peak scattering angle with particle size.

FIG. 5 shows the relationship between the particle diameter $D_p$ and the peak scattering angle $\theta^*$ at which $i_2(\theta)\theta$ has the peak. The maximum of $\theta^*$ is 37.44 degrees. It is clear that all possible $\theta^*$ can be covered by a common convergent lens for the determination of size distribution of a group of particles with size distribution.

Particle size can be determined also from the ratio or the difference between scattered intensities $I_1(\theta)$ and $I_2(\theta)$. In this case, however, the difference in the intensities of the two polarized components of the scattered light rather increases with scattering angle and is maximum at an angle around 90 degrees. Therefore, it is apparent that intensities at higher scattering angles beyond 37.4 degrees may be used to improve the accuracy of sizing.

It is to be noted that, for a mixture in which fine particles are mixed with large particles, the size distribution of the fine particles can be measured more precisely according to the present method.

As described above, the difference between $I_2(\theta)$ and $I_1(\theta)$, the scattered intensities on the plane of the polarization and on the plane vertical thereto, respectively, is due to scattering from the fine particles. The scattered intensities $I_1(\theta)$ and $I_2(\theta)$ are expressed by the following equations, wherein $D^*$ represents the particle size at which the difference between the polarized components of the scattered intensities, $i_2(D,\theta)$ and $i_1(D,\theta)$, for a particle of a diameter D, can be neglected, $N_1(D)$ being the number of particles of size smaller than the aforesaid limiting size $D^*$, and $N_2(D)$ the number of particles of size larger than aforesaid limiting size.

$$I_1(\theta) = \int_0^{D^*} i_1(D,\theta)N_1(D)dD + \int_{D^*}^{\infty} i_1(D,\theta)N_2(D)dD \quad (1)$$

$$I_2(\theta) = \int_0^{D^*} i_2(D,\theta)N_1(D)dD + \int_{D^*}^{\infty} i_2(D,\theta)N_2(D)dD \quad (2)$$

Thus, the difference therebetween is given by $$I_1(\theta) - I_2(\theta) = \int_0^{D^*} \{i_1(D,\theta) - i_2(D,\theta)\}N_1(D)dD \quad (3)$$

Based on this equation, the size distribution of the fine particles $N_1(D)$ is obtained.

The size distribution is determined so that the difference between the measured intensity profile and the one theoretically calculated for the size distribution by the above equation is minimized.

Figure 6:
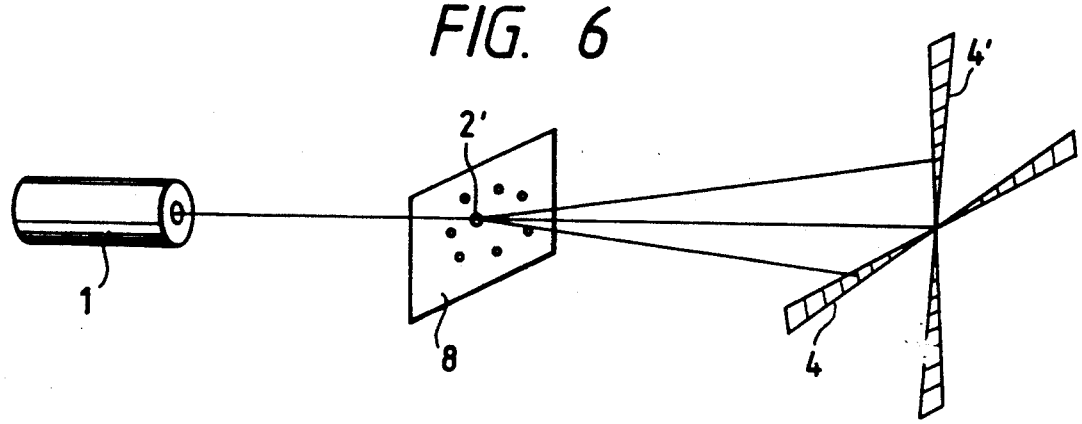

FIG. 6 shows another embodiment in which fine particles are sampled on a transparent substrate (8) and an parallel polarized beam of a small size illuminates a single particle (2'). The scattered light is directly detected by the array (4 and 4') of photoelectric conversion elements, and the necessary information is outputted via a signal processing circuit in a manner similar to that as described above.

The method described above can be applied also to the sizing of a group of particles of which spatial extent along the incident beam is very small. In this application an apparatus without the convergent lens can be used for the measurement of the scattered intensities. The size distribution of particles floating in a fluid flowing in a very narrow channel or in a fine tube can be also determined.

This invention can provide an apparatus for optically determining the size of a single fine particle and the size distribution of a group of fine particles which are comparable to or smaller than the wavelength of light with high accuracy. In addition, this invention has the following marked merits:

(1) The minimum size that can be measured by the present method is very small as compared with that by the present diffraction-based method, and the dynamic range (the ratio of the maximum and the minimum sizes that can be determined) is extended by more than 10 times.

(2) The size distribution of fine particles mixed with large particles can be accurately determined by analyzing the difference between the distributions of scattered intensities on the plane of polarization and on the plane vertical thereto, because the difference is produced only by the fine particles.

(3) The maximum of the peak scattering angle $\theta^*$ is 37.44 degrees, so that even for ultra fine particles, all possible θ* can be covered by a common convergent lens. Therefore, the construction and the cost of the apparatus almost remain unchanged, with maintaining the merits of good reproducibility and operability.

What is claimed is:

1. A method for determining the size of a single fine particle and the size distribution of a group of fine particles, comprising the steps of:
   (a) providing a parallel polarized beam having a single wavelength and a plane of polarization;
   (b) directing said parallel polarized beam against at least a single fine particle to be measured to cause scattering of said parallel polarized beam;
   (c) detecting the intensity of the scattered said parallel polarized beam at a plurality of locations as a function of a scattering angle between said parallel polarized beam and the respective one of said plurality of locations;
   (d) calculating a product for each of said plurality of locations of the measured intensity at each said location times the angle between said parallel polarized beam and the respective said location; and
   (e) determining the size of the particle from said product calculated in step (d).

2. A method for determining the particle size according to claim 1, wherein in step (e) the size of a single fine particle is determined by calculation of the scattering angle at which said product has a maximum value.

3. A method for determining the particle size according to claim 1, wherein in step (e), further comprising the step of determining the size distribution of a plurality of fine particles from analysis of the variation of said product as a function of the scattering angle.

4. A method for determining size according to claim 1, wherein in step (b), directing said parallel polarized beam having a single wavelength against a group of particles to be measured, and in step (e), determining the distribution of particle sizes from the ratio between the scattered intensities on said plane of polarization and on a plane at a right angle to said plane of polarization.

5. A method for determining size according to claim 1, wherein in step (b), said parallel polarized beam having a single wavelength is directed against a group of particles to be measured, and in step (e), further comprising determining the distribution of particle sizes from the difference between the scattered intensities on said plane of polarization and on a plane at a right angle to said plane of polarization.

6. A method as claimed in claim 1, wherein the particle whose diameter is to be detected has a diameter which is smaller than said wavelength of said parallel polarized beam.

7. An apparatus for determining the distribution of particle size, comprising:

a light source for generating a parallel polarized beam to be impinge on at least one particle to cause scattering of said parallel polarized beam; the parallel polarized beam having a single wavelength as well as a central axis and a plane of polarization;

a first array of first photodetecting elements aligned with said plane of polarization of said parallel polarization beam for detecting the intensity of scattered radiation impinging on respective ones of said first photodetecting elements, respective said first photodetecting elements being at respective scattering angles from the central axis of said parallel polarized beam;

a second array of second photodetecting elements aligned in a plane which is substantially perpendicular to said first array and to said plane of polarization for detecting the intensity of scattered radiation impinging on respective ones of said second photodetecting elements, respective said second photodetecting elements being at respective scattering angles from the central axis of said parallel polarized beam; and calculating means for processing output signals from said first array of first photodetecting elements and said second array of second photodetecting elements for computing, for each respective location of respective ones of said first and second photodetecting elements, respective products of the scattering angle at the respective location times the detected intensity at the respective location, and for determining a particle diameter by comparing said products as a function of the scattering angle.

8. An apparatus as claimed in claim 7, wherein the particle whose diameter is to be detected has a diameter which is smaller than said wavelength of said parallel polarized beam.

* * * * *